(12) United States Patent
Wang et al.

(10) Patent No.: US 11,333,653 B2
(45) Date of Patent: May 17, 2022

(54) METHOD FOR EVALUATING CREASE RECOVERY OF FABRICS BASED ON POWER FUNCTION EQUATION

(71) Applicant: Jiangnan University, Jiangsu (CN)

(72) Inventors: Lei Wang, Jiangsu (CN); Weidong Gao, Jiangsu (CN)

(73) Assignee: Jiangnan University, Wuxi (CN)

( * ) Notice: Subject to any disclaimer, the term of this patent is extended or adjusted under 35 U.S.C. 154(b) by 530 days.

(21) Appl. No.: 16/536,870

(22) Filed: Aug. 9, 2019

(65) Prior Publication Data

US 2020/0326323 A1 Oct. 15, 2020

(30) Foreign Application Priority Data

Apr. 9, 2019 (CN) .......................... 201910278190.6
Jun. 10, 2019 (CN) .......................... 201910495039.8

(51) Int. Cl.
*G06K 9/00* (2022.01)
*G01N 21/86* (2006.01)
*G01N 33/36* (2006.01)
*G01B 11/26* (2006.01)
*H04N 5/225* (2006.01)
*H04N 7/18* (2006.01)
*G06V 20/40* (2022.01)

(52) U.S. Cl.
CPC ........... *G01N 33/367* (2013.01); *G01B 11/26* (2013.01); *G06V 20/46* (2022.01); *H04N 5/2253* (2013.01); *H04N 7/183* (2013.01)

(58) Field of Classification Search
USPC ....... 382/100, 103, 106, 108, 111, 168, 173, 382/181, 199, 214, 254, 276, 286, 305; 250/559.07, 559.04
See application file for complete search history.

(56) References Cited

U.S. PATENT DOCUMENTS

| | | | | |
|---|---|---|---|---|
| 7,601,978 B2* | 10/2009 | Sari-Sarraf | .............. | D06H 3/08 250/559.07 |
| 2019/0176176 A1* | 6/2019 | Roberts | .................. | B05B 11/30 |
| 2019/0194863 A1* | 6/2019 | Xu | ............. | D06L 4/13 |
| 2020/0256009 A1* | 8/2020 | Altman | ................. | D06M 15/15 |
| 2021/0239892 A1* | 8/2021 | Iwasaki | .................. | B32B 27/08 |
| 2021/0269968 A1* | 9/2021 | Fu | ............. | B32B 5/14 |
| 2021/0380783 A1* | 12/2021 | Gordon | .................... | D01F 2/00 |

FOREIGN PATENT DOCUMENTS

| | | |
|---|---|---|
| CN | 102998253 A | 3/2013 |
| CN | 106198937 A | 12/2016 |
| CN | 107064143 A | 8/2017 |

* cited by examiner

*Primary Examiner* — Seyed H Azarian

(74) *Attorney, Agent, or Firm* — Muncy, Geissler, Olds & Lowe, P.C.

(57) ABSTRACT

A method for evaluating crease recovery of fabrics based on power function equation. The steps are: (1) place the sample in the sample placement area; (2) pressure the overlapping part of the sample; (3) let the free part of the sample automatically restore and record the video image of the sample crease recovery by camera; (4) process the video image of the fabric crease recovery and calculating the recovery angle of each frame of video image; (5) repeat steps 1 to 4 to measure N samples of the same fabric; (6) obtain the dynamic process of fabric crease recovery angle change. This can reveal which type of fabric has better recovery property, when the existing methods have the similar results of recovery angle.

3 Claims, 1 Drawing Sheet

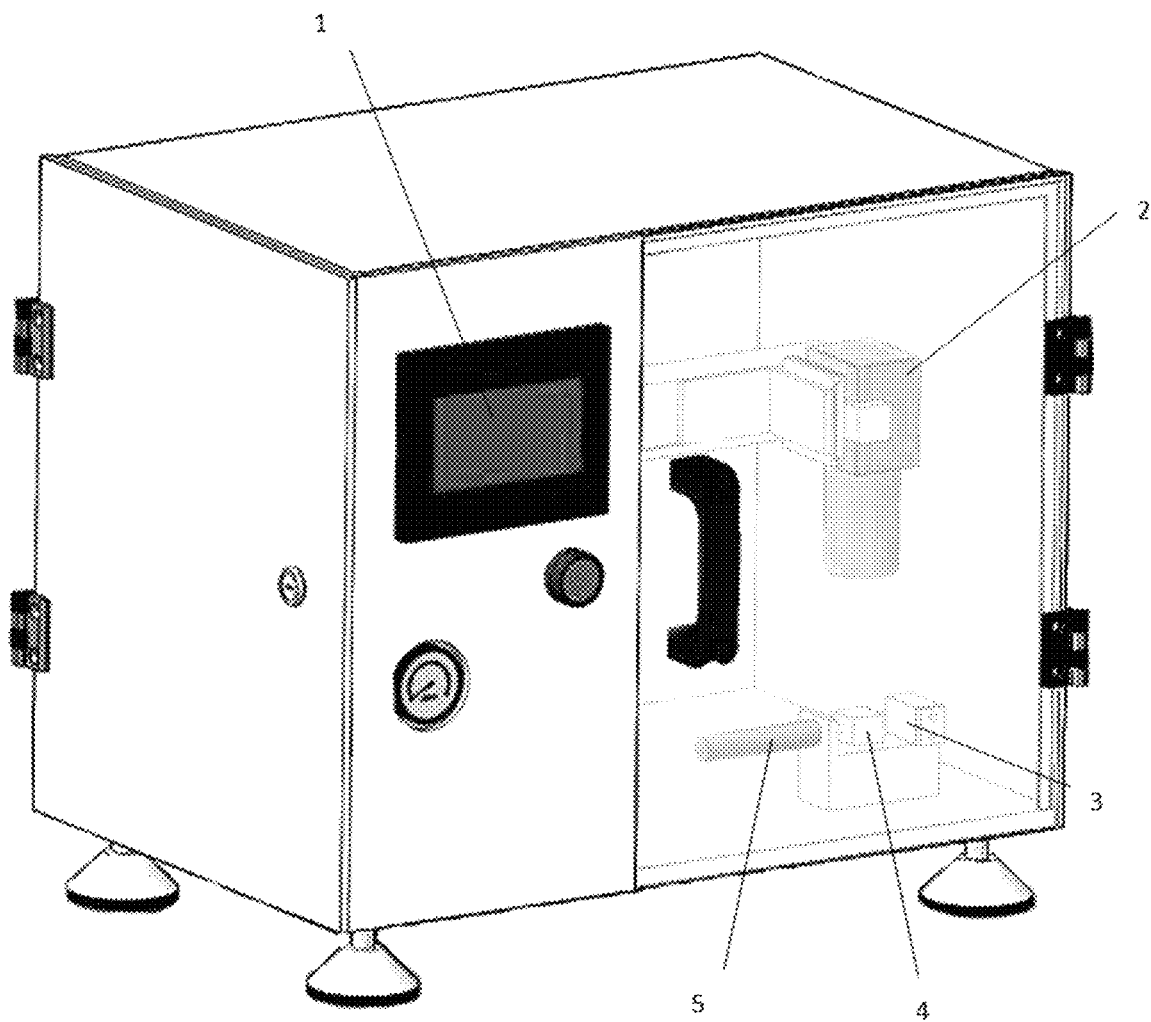

METHOD FOR EVALUATING CREASE RECOVERY OF FABRICS BASED ON POWER FUNCTION EQUATION

TECHNICAL FIELD

The invention belongs to the field of textile performance testing, and specifically relates to a method for evaluating crease recovery of fabrics based on power function equation.

BACKGROUND

The crease recovery property of a fabric directly affects its appearance and performance. At present, the main standard methods based on recovery angle are ISO 2313-1972 (Textiles—Determination of the recovery from creasing of a horizontally folded sample of fabric by measuring the angle of recovery), AATCC 66-2014 (Wrinkle recovery of woven fabrics: recovery angle) and GB/T 3819-1997 (Textile fabrics-Determination of the recovery from creasing of a folded sample by measuring the angle of recovery). In these methods, samples of specified size were pressured under a fixed weight hammer for 5 min, and freely recovery after the pressure was released, then the recovery angle on the 5 min in the recovery period was measured to assess the fabric crease recovery property. At present, main test instruments for evaluating fabric crease recovery property are Shirley crease recovery tester, YG541 digital crease recovery tester and so on.

The main problems of existing testing methods are as follows: (1) In the process of testing, a pressurized sample is necessary to be transferred from a loading device to a recovery angle measurement device to have angle measurement. This procedure is easily disturbed by human or environmental factors, and has a low automation degree. Only the recovery angle is used as an index to evaluate the crease recovery property of fabrics. Thus this evaluation method is one-sided. (2) It is impossible to obtain the initial recovery status (within 5s or 10s) when the pressure is release, for the sample needs to be transferred between pressing and testing procedure. (3) The existing methods only measure the static recovery angle after a certain recovery time, and cannot fully reflect the recovery performance of the sample in the whole recovery process. For example, two fabrics have the same recovery angle at 5 min in the recovery period. However, in the recovery process, the recovery angle at 1 min of one of the fabrics is close to the angle at 5 min, while the recovery angle of the other fabric gradually increases. Furthermore, the existing method limits the establishment of evaluation system for crease recovery property.

The patent (CN102998253A), a dynamic measurement and characterization method of fabric wrinkle recovery angle, uses the standard heavy object to press a sample and manual transfer the sample to measure the recovery angle after pressure relief. However, it cannot obtain the recovery angle at the initial stage of recovery period, nor can it realize the output of the recovery angle data in the whole process of crease recovery, and can only be evaluated by the recovery angle after a period of time. The patent does not propose indicator parameter to characterize the crease recovery of fabrics.

The patent (CN106198937A), a dynamic evaluation method of fabric crease recovery performance, and the patent (CN107064143A), a characterization system of wool fabric crease recovery process, obtained the angle change of a fabric in the crease recovery process, and used piecewise function to extract the parameters reflecting the recovery situation of initial stage, rapid recover stage and slow recover stage. The linear equation y=ax+b was used in the initial stage. The equation $y=ax^b+C$ is used to evaluate the rapid recover stage, and the specific time recovery angle is used to evaluate the slow recover stage. This evaluation method requires a high frame rate for video image acquisition in fabric crease recovery process, which requires a large amount of calculation and takes a long time to process. The fitting equation of the rapid recover stage can not reflect the physical meaning of the actual crease recovery of the fabric; the multi-index evaluation of the fitting results by using multiple formulas fails to put forward comprehensive indicators and fails to reflect the speed at which the sample recovers to stable state in the recovery process. Thus the evaluation results are not visual and reliable.

SUMMARY OF THE INVENTION

In view of the above problems, the present invention provides a method for evaluating crease recovery of fabrics based on power function equation, according to the physical properties of fabric crease recovery. The video image of fabric crease recovery is processed by computer, from which the recovery angle at each time in the recovery period is obtained. From the data of the recovery angle varying with time, a power function fitting of the recovery angle varying with time is calculated. A new index for evaluating the crease recovery property of fabrics is proposed based on the physical meaning of the equation coefficient. The index realizes the accurate and comprehensive evaluation of the crease recovery property of fabrics.

According to the technical solution provided by the present invention, the video image of the fabric crease recovery process is collected to realize the detection of the recovery angle of each frame image. Through data analysis technology, the equation of time-recovery angle curve is fitted from the trend of recovery angle changing with time, from which the physical meaning of equation coefficients is analyzed. This method can accurately evaluate fabric crease recovery process.

The technical solution of the present invention is as follows:

A fabric crease recovery device for testing the crease recovery of fabrics comprises a numerical control (NC) interface system, a camera, a sample placement area, a pressing block and a pressurized cylinder. The NC interface system is connected with the pressurized cylinder and the camera, which can accurately adjust the pressurized time and pressure of the pressurized cylinder. The pressurized cylinder is connected with the pressing block. The pressing block is placed on the upper surface of the sample placement area. The sample placement area realizes the function of fixing the sample. The pressurized cylinder drives the pressing block to move toward or away from the sample placement area. When the pressing block moves toward the sample placement area, the pressing block causes the folded sample to be compressed for a certain time under constant pressure, and the sample will be creased; when the pressing block moves away from the sample placement area, the recovery angle formed by the fixed part and the free part of the sample gradually increases with the recovery of creases. The camera is located right above the sample placement area. The camera collects video images of the sample crease recovery process and transmits them to the NC interface system for image processing and recovery angle calculation.

The NC interface system comprises video image processing software system and evaluation index extraction system. The video image processing software system realizes the output of the angle value of each video image frame. The main processing steps are video single frame image extraction, image binarization, morphological operation and recovery angle calculation. The evaluation index extraction system realizes the output of power function fitting equation for the "time-average recovery angle" obtained from the average recovery angle at the corresponding time after repeated test, and then extracts coefficients of the power function equation. By calculating the coefficient of equation, the sub-item index of fabric crease recovery is obtained. Then, the composite index of fabric crease recovery can be calculated by the average value of the sub-item indexes with different folding modes, that is, the index for evaluating fabric crease recovery property.

A method for evaluating crease recovery of fabrics based on power function equation, the steps are as follows:

Step 1: Pressure and time are set in the NC interface system. The sample is placed in the sample placement area. One part of the sample is fixed in the sample placement area, and the other part of the sample bends and overlaps the fixed part.

Step 2: The pressurized cylinder controls the pressing block to push towards the sample placement area, and pressurizes the overlapping part of the sample.

Step 3: When the pressure time set by the NC interface system is reached, the pressurized cylinder controls the movement of the pressing block away from the sample placement area, so that the free part of the sample can automatically recover. At the same time, the camera records the video image of the sample crease recovery.

Step 4: Process the fabric crease recovery video image. Calculate the recovery angle of each frame of video image.

Step 5: Repeat steps 1 to 4 to measure N samples with the same folding mode of the same fabric And to obtain the average value of the recovery angle of N samples with the same recovery time. Thus, obtain the "time-average recovery angle" data.

When N=3, the recovery angle at the first second of sample 1 is $m_1$, the recovery angle at the first second of sample 2 is $m_2$, and the recovery angle at the first second of sample 3 is $m_3$, then the average value of recovery angle at the first second of the fabric is $\overline{m_1}=(m_1+m_2+m_3)/3$. Similarly, the data of the change of the recovery angle of the fabric with time can be obtained. The measured value of recovery angle at t time is $\overline{m_t}$.

Step 6: The dynamic process of fabric crease recovery angle change is obtained by image processing algorithm. The "time-average recovery angle" data are fitted into power function equation by using non-linear curve fitting method.

$$f(t)=at^b \quad (1)$$

In the equation, t represents time, and f(t) represents the recovery angle.

The fitting function of the non-linear curve is shown in equation (2), and the initial values of a and b are set to be 10 and 0.1 according to experience. The initial value is based on the empirical data obtained from experiments on different fabrics. Through analysis, a is related to the initial recovery speed. In consideration of the relationship with the physical properties of fabric resilience, the initial recovery speed of general textile materials is between tens and hundreds degrees, and b is between 0 and 0.1. When the initial value or the data close to the initial value is used as the initial value of fitting, the number of iterations for calculating the parameters of the fitting equation can be shortened and the results can be obtained more quickly.

$$\min_i \|f(t)-\overline{m_t}\|_2^2 = \min_i \Sigma_t(f(t)-\overline{m_t})^2 \quad (2)$$

According to equation (2), two coefficients a and b in equation (1) are obtained so that the minimum binary expression of formula (2) is established.

Wherein, the first coefficient a in equation (1) is equal to the angle value of fabric crease recovery at the first unit time in the recovery period, reflecting the initial recovery degree of the sample. The larger the value of a is, the better the recovery property of the sample is.

The second coefficient b in equation (1) is equal to the ratio of the instantaneous recovery speed at the end of the first unit time of recovery stage to the angle value of fabric crease recovery at the first unit time. It is defined as the recovery index, which reflects the speed at which the sample recovers to a stable state. The smaller the value of b is, the better the recovery property of the sample is.

Step 7: Extract the index to evaluate the crease recovery performance of the corresponding folded sample from equation (1). A new coefficient K is constructed by the values of coefficients a and b to evaluate the crease recovery properties of the samples folded by the corresponding ways.

$$K = \frac{a}{b} \quad (3)$$

Step 8: The average value of the sub-index $K_1$, $K_2$, $K_3$ and $K_4$ corresponding to the four folding modes of fabric samples (warp face-to-face folded, warp back-to-back folded, weft face-to-face folded and weft back-to-back folded) is calculated. As the comprehensive evaluation index, $\overline{K}$ demonstrates the crease recovery property of the whole fabric and is called the comprehensive index of fabric crease recovery.

The beneficial effect of the present invention is that the invention can provide an effective and comprehensive method for evaluating fabric crease recovery. Based on the "time-average recovery angle" and power function equation fitting of fabric sample dynamic recovery angle change during testing process, the physical meaning of power function equation coefficient is excavated, a new index for characterizing fabric crease recovery property is constructed and the comprehensive index of fabric crease recovery is adopted. This method is more feasible and effective. This method can reveal which type of fabric has better recovery property, when the existing methods have the similar results of recovery angle.

DESCRIPTION OF DRAWINGS

The sole FIGURE is a schematic diagram of the present invention.

In the FIGURE, 1 NC interface system; 2 camera; 3 sample placement areas; 4 pressing block; 5 pressurized cylinder.

DETAILED DESCRIPTION

The present invention is described combining with the technical solution and the FIGURE.

As shown in the FIGURE, the present invention presents a method for evaluating crease recovery of fabrics based on power function equation. The steps are as follows:

Step 1: Pressure and time are set in the NC interface system. The sample is placed in the sample placement area 3 to form a bending and overlapping state. One part of the sample is fixed in the sample placement area 3. Open the tester.

Step 2: Pressurized cylinder 5 controls the pressing block 4 to push toward sample placement area 3, and then pressurizes the sample.

Step 3: When the pressure time set by the NC interface system is reached, the pressurized cylinder 5 controls the movement of the pressing block 4 away from the sample placement area 3, so that the free part of the sample can automatically recover. At the same time, the camera 2 records the video image of the sample crease recovery.

Step 4: The computer processes the video image of fabric crease recovery, calculates the recovery angle of each video image frame, and realizes the full characterization of the change of fabric crease recovery angle.

Step 5: The dynamic process of fabric crease recovery angle is obtained by image processing algorithm, and the data of fabric crease recovery angle is fitted to power function equation.

$$f(t)=at^b \qquad (2)$$

In the equation, t is time, f(t) is the recovery angle.

Step 6: Extract the index for evaluating fabric crease recovery performance from Equation (1). Wherein, index a represents the initial recovery angular displacement (the larger the a is, the faster the initial recovery is; the smaller the a is, the slower the initial recovery is). Index b represents the recovery exponent (the larger the b is, the longer the recovery process is; the smaller the b is, the shorter the recovery process is).

Step 7: Calculate the sub-item index K of fabric crease recovery of each folding mode by coefficient a and b. The sub-item index of fabric crease recovery for four folding modes, i.e. warp face-to-face folded, warp back-to-back folded, weft face-to-face folded and weft back-to-back folded, can be used to find the average number and obtain the comprehensive index of fabric crease recovery.

Ten kinds of fabrics were tested, and the fabric specifications are listed in Table 1.

TABLE 1

| Fabric parameters | | | | | | |
|---|---|---|---|---|---|---|
| | | | Yarn count/tex | | Yarn density/(numbers · (10 cm)$^{-1}$) | |
| Fabric | Material | Weave | Warp | Weft | Warp | Weft |
| A | 100% Cotton | Plain | 14.6 | 15.8 | 555 | 568 |
| B | 100% Cotton | 3/1 ↖ Twill | 29.2 | 64.8 | 465 | 200 |

The above fabrics were treated by four post-finishing processes as shown in Table 2. Including the fabric without post-finishing, there were totally 10 types of samples. The corresponding relationship between sample number and fabrics is shown in Table 3.

TABLE 2

| Post-finishing method | |
|---|---|
| No. | Post-finishing method |
| 1 | Soft Finishing |
| 2 | 6% Resin finishing (with softener) |
| 3 | 12% Resin finishing (with softener) |
| 4 | 18% Resin finishing (with softener) |

TABLE 3

| Sample number | | |
|---|---|---|
| Sample number | Fabric type | Post-finishing method |
| 1# | A | No post-finishing |
| 2# | A | Soft Finishing |
| 3# | A | 6% Resin finishing (with softener) |
| 4# | A | 12% Resin finishing (with softener) |
| 5# | A | 18% Resin finishing (with softener) |
| 6# | B | No post-finishing |
| 7# | B | Soft Finishing |
| 8# | B | 6% Resin finishing (with softener) |
| 9# | B | 12% Resin finishing (with softener) |
| 10# | B | 18% Resin finishing (with softener) |

According to the method described above, the crease recovery properties of fabrics are tested and the results are listed in Table 4. Coefficient a and b are constants in the power function fitting equation of "time-average recovery angle". $R^2$ is the resolvable coefficient of goodness of fit. K is the sub-item index of fabric crease recovery, $\overline{K}$ is the composite index of fabric crease recovery. $F_t$ and $F_c$ are measured and calculated values at the 5th minute of the recovery stage respectively. ΔF is the difference between $F_t$ and $F_c$. $F_{jw}$ is the evaluation index of the existing standard method (The sum of warp and weft crease recovery angles).

TABLE 4

| Test results | | | | | | | | | | |
|---|---|---|---|---|---|---|---|---|---|---|
| Sample number | Folding mode | a | b | $R^2$ | K | $\overline{K}$ | $F_t/°$ | $F_c/°$ | $\Delta F/°$ | $F_{jw}/°$ |
| 1# | Warp face-to-face | 46.8 | 0.0740 | 0.976 | 632.1 | 689.3 | 70.7 | 71.4 | 0.7 | 149.0 |
| | Warp back-to-back | 46.5 | 0.0755 | 0.972 | 616.1 | | 70.7 | 71.5 | 0.9 | |
| | Weft face-to-face | 51.2 | 0.0699 | 0.983 | 732.3 | | 75.4 | 76.3 | 0.9 | |
| | Weft back-to-back | 54.7 | 0.0704 | 0.986 | 776.5 | | 81.1 | 81.7 | 0.6 | |

TABLE 4-continued

| | | Test results | | | | | | | | | |
|---|---|---|---|---|---|---|---|---|---|---|---|
| Sample number | Folding mode | a | b | $R^2$ | K | $\overline{K}$ | $F_t/°$ | $F_c/°$ | $\Delta F/°$ | $F_{jw}/°$ |
| 2# | Warp face-to-face | 51.7 | 0.0759 | 0.974 | 680.8 | 850.3 | 78.7 | 79.7 | 0.9 | 173.0 |
| | Warp back-to-back | 62.0 | 0.0622 | 0.978 | 995.6 | | 87.3 | 88.4 | 1.1 | |
| | Weft face-to-face | 62.3 | 0.0694 | 0.989 | 898.4 | | 91.7 | 92.6 | 0.8 | |
| | Weft back-to-back | 59.4 | 0.0719 | 0.964 | 826.3 | | 88.2 | 89.6 | 1.4 | |
| 3# | Warp face-to-face | 92.5 | 0.0539 | 0.957 | 1718.1 | 1649.4 | 124.7 | 125.8 | 1.2 | 240.1 |
| | Warp back-to-back | 91.0 | 0.0566 | 0.953 | 1608.3 | | 124.3 | 125.6 | 1.3 | |
| | Weft face-to-face | 88.4 | 0.0521 | 0.966 | 1697.9 | | 118.0 | 119.0 | 1.1 | |
| | Weft back-to-back | 84.3 | 0.0536 | 0.962 | 1573.2 | | 113.1 | 114.4 | 1.3 | |
| 4# | Warp face-to-face | 97.6 | 0.0499 | 0.931 | 1956.1 | 2097.5 | 128.2 | 129.7 | 1.5 | 258.8 |
| | Warp back-to-back | 102.6 | 0.0457 | 0.952 | 2246.3 | | 131.9 | 133.1 | 1.2 | |
| | Weft face-to-face | 98.4 | 0.0479 | 0.971 | 2054.8 | | 128.3 | 129.4 | 1.1 | |
| | Weft back-to-back | 99.9 | 0.0469 | 0.945 | 2132.9 | | 129.2 | 130.5 | 1.3 | |
| 5# | Warp face-to-face | 109.1 | 0.0419 | 0.953 | 2601.2 | 2811.4 | 137.6 | 138.6 | 1.0 | 276.6 |
| | Warp back-to-back | 113.7 | 0.0389 | 0.916 | 2923.9 | | 140.7 | 141.9 | 1.2 | |
| | Weft face-to-face | 111.4 | 0.0391 | 0.951 | 2847.4 | | 138.2 | 139.2 | 1.0 | |
| | Weft back-to-back | 110.5 | 0.0385 | 0.942 | 2873.0 | | 136.6 | 137.6 | 1.1 | |
| 6# | Warp face-to-face | 35.0 | 0.0698 | 0.963 | 502.2 | 805.4 | 51.4 | 52.2 | 0.7 | 148.5 |
| | Warp back-to-back | 53.1 | 0.0658 | 0.980 | 807.3 | | 76.5 | 77.3 | 0.8 | |
| | Weft face-to-face | 66.3 | 0.0622 | 0.963 | 1066.0 | | 93.4 | 94.6 | 1.2 | |
| | Weft back-to-back | 53.6 | 0.0634 | 0.938 | 846.2 | | 75.7 | 77.0 | 1.2 | |
| 7# | Warp face-to-face | 36.2 | 0.1016 | 0.982 | 356.3 | 916.7 | 63.8 | 64.6 | 0.8 | 181.3 |
| | Warp back-to-back | 70.2 | 0.0665 | 0.980 | 1054.4 | | 101.6 | 102.6 | 1.0 | |
| | Weft face-to-face | 85.9 | 0.0575 | 0.913 | 1494.1 | | 117.6 | 119.2 | 1.6 | |
| | Weft back-to-back | 53.9 | 0.0707 | 0.961 | 761.9 | | 79.6 | 80.7 | 1.1 | |
| 8# | Warp face-to-face | 59.5 | 0.0762 | 0.947 | 780.7 | 1370.1 | 90.3 | 91.8 | 1.5 | 223.2 |
| | Warp back-to-back | 89.9 | 0.0573 | 0.971 | 1568.7 | | 123.3 | 124.6 | 1.3 | |
| | Weft face-to-face | 98.5 | 0.0516 | 0.970 | 1911.2 | | 130.9 | 132.2 | 1.4 | |
| | Weft back-to-back | 73.1 | 0.0599 | 0.945 | 1219.9 | | 101.8 | 102.9 | 1.1 | |
| 9# | Warp face-to-face | 84.8 | 0.0508 | 0.903 | 1669.3 | 1987.6 | 112.2 | 113.3 | 1.1 | 244.4 |
| | Warp back-to-back | 99.3 | 0.0464 | 0.957 | 2140.1 | | 128.0 | 129.3 | 1.3 | |
| | Weft face-to-face | 109.0 | 0.0420 | 0.961 | 2594.4 | | 137.1 | 138.5 | 1.4 | |
| | Weft back-to-back | 83.2 | 0.0538 | 0.946 | 1546.5 | | 111.4 | 113.0 | 1.6 | |
| 10# | Warp face-to-face | 93.3 | 0.0424 | 0.915 | 2199.9 | 3019.0 | 117.4 | 118.8 | 1.4 | 273.2 |
| | Warp back-to-back | 121.3 | 0.0367 | 0.939 | 3300.7 | | 148.2 | 149.5 | 1.4 | |
| | Weft face-to-face | 121.8 | 0.0380 | 0.971 | 3204.4 | | 150.2 | 151.2 | 1.0 | |
| | Weft back-to-back | 109.4 | 0.0325 | 0.947 | 3371.1 | | 130.6 | 131.7 | 1.1 | |

From the data in Table 4, it can be concluded that:

(1) $R^2$ of the fitting equation is larger than 0.9, which shows that the "time-average recovery angle" equation has a high fitting accuracy.

(2) The new evaluation index $\overline{K}$ shows a positive correlation with $F_{jw}$ (r=0.94), which indicates that the proposed $\overline{K}$ value is feasible to characterize the crease recovery property of fabrics.

(3) The new evaluation index $\overline{K}$ is more effective in judging the crease recovery property of fabrics. For example, the $F_{jw}$ values of Sample 1 # and Sample 6 # are 149.0° and 148.5° respectively, which are close with each other. It is difficult to judge the crease recovery properties of these two fabrics according to the existing method. But the new indexes K are 689.3 and 805.4 respectively, it is easy to distinguish that the crease recovery properties of Sample 6 # are better than that of Sample 1 #. Similarly, for Sample 5 # and Sample 10 #, $F_{jw}$ is 276.6° and 273.2° respectively, while the new index K is 2811.4 and 3019.0 respectively. It is easy to distinguish that the crease recovery performance of Sample 10 # is better than that of Sample 5 #.

The invention claimed is:

1. A method for evaluating crease recovery of fabrics based on power function equation wherein the following steps are comprised:

step 1: pressure and time are set in the numerical control (NC) interface system; the sample is placed in the sample placement area; one part of the sample is fixed in the sample placement area; the other part of the sample bends and overlaps the fixed part;

step 2: the pressurized cylinder controls the pressing block to push towards the sample placement area and pressurizes the overlapping part of the sample;

step 3: when the pressure time set by the NC interface system is reached, the pressurized cylinder controls the movement of the pressing block away from the sample placement area, so that the free part of the sample can automatically recover, and the camera records the video image of the sample crease recovery;

step 4: process the video image of fabric crease recovery and calculate the recovery angle of each frame of video image;

step 5: repeat steps 1 to 4 to measure N samples of the same fabric and find the average recovery angle of N samples at the same recovery time;

step 6: the dynamic process of fabric crease recovery angle change is acquired by image processing algorithm; the data of recovery angle in the recovery process are fitted into power function equation by non-linear curve fitting method:

$$f(t) = at^b \quad (1)$$

in the equation, t stands for time and f(t) represents recovery angle;

the fitting function of the non-linear curve is shown in equation and the initial values of a and b are set to be 10 and 0.1 respectively, $$\min_t \|f(t) - \overline{m_1}\|_2^2 = \min \Sigma_t (f(t) - \overline{m_1})^2 \quad (2)$$

coefficients a and b in equation are obtained according to equation so that the minimum binary expression of equation is established;

step 7: the first and second coefficients for evaluating the crease recovery properties of fabrics are extracted from equation;

wherein, the first coefficient is a in equation is equal to the angle value of fabric crease recovery at the first unit time after the beginning of recovery, and the second coefficient is b in equation is equal to the ratio of instantaneous recovery speed at the end of the first unit time of recovery stage to the angle value of fabric crease recovery at the first unit time, and is defined as recovery index;

the coefficient K is constructed by the values of coefficient a and b, and the crease recovery property of the fabric is evaluated thereby;

$$K = \frac{a}{b} \quad (3)$$

step 8, the average value $\overline{K}$ of sub-indexes $K_1$, $K_2$, $K_3$ and $K_4$ corresponding to the four folding modes of fabric samples are obtained; as a comprehensive evaluation index, it reflects the crease recovery property of the whole fabric, which is called the comprehensive index of fabric crease recovery.

2. The method for evaluating crease recovery of fabrics based on power function equation according to claim 1, wherein in step 8, the four folding modes include warp face-to-face folded, warp back-to-back folded, weft face-to-face folded and weft back-to-back folded.

3. The method for evaluating crease recovery of fabrics based on power function equation according to claim 1, a fabric crease recovery device is used in the method; the fabric crease recovery device comprises a numerical control interface system, a camera, a sample placement area, a pressing block and a pressurized cylinder; the NC interface system is connected with the pressurized cylinder and the camera to realize the precise adjustment of the pressurized time and pressure of the pressurized cylinder; the pressurized cylinder is connected with the pressing block, the pressing block is placed on the upper surface of the sample placement area, the sample placement area realizes the function of fixing the sample, and the camera is positioned right above the sample placement area; the camera collects video images of the sample crease recovery process and transmits them to the NC interface system.

* * * * *